(12) United States Patent
Levorse et al.

(10) Patent No.: US 7,547,668 B1
(45) Date of Patent: *Jun. 16, 2009

(54) DIOXASPIRO COMPOUNDS AND THEIR USE IN PERFUME COMPOSITIONS

(75) Inventors: Anthony T. Levorse, Westfield, NJ (US); Richard A. Weiss, Livingston, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/960,143

(22) Filed: Dec. 19, 2007

(51) Int. Cl.
*C11D 3/50* (2006.01)
(52) U.S. Cl. .................. 510/103; 512/9; 549/331; 549/341
(58) Field of Classification Search ................. 510/103; 512/9; 549/331, 341
See application file for complete search history.

(56) References Cited

FOREIGN PATENT DOCUMENTS

DE          2533048      *   2/1977

OTHER PUBLICATIONS

Meier, L. et al. "A New Synthesis of 4,5-Unsubstituted 1,3-Dioxoles" Synthesis (1987) 5: 517-520.

Dann, A.E. et al. "Rapid and Convenient Technique for Converting Ketones into Their Ethylenedioxy-Derivatives or Trimethylenedioxy-Derivatives, and for Making Acetonides" Journal of the Chemical Society-Perkin Transactions 1: Organic and Bio-organic Chemistry (1979) 1: 158-160.

* cited by examiner

*Primary Examiner*—John R Hardee
(74) *Attorney, Agent, or Firm*—Elizabeth M. Quirk; XuFan Tseng; Joseph F. Leightner

(57) ABSTRACT

The present invention a method of improving, enhancing or modifying a fragrance formulation through the addition of an olfactory acceptable amount of the following compound:

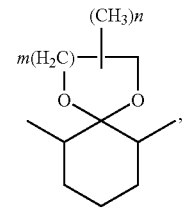

wherein m is 1 or 2;
and if m is 1, which provides a five-membered dioxaspiro ring, n is an integer from 2 to 4, and the methyl group in the dioxaspiro ring is independently located in the 2 and/or 3 positions of the dioxaspiro ring;
or if m is 2, which provides a six-membered dioxaspiro ring, n is an integer from 0 to 6, and the methyl group in the dioxaspiro ring is independently located in the 2, 3, and/or 4 positions of the dioxaspiro ring.

17 Claims, No Drawings

DIOXASPIRO COMPOUNDS AND THEIR USE IN PERFUME COMPOSITIONS

FIELD OF THE INVENTION

The present invention relates to new chemical entities and the incorporation and use of the new chemical entities as fragrance materials.

BACKGROUND OF THE INVENTION

There is an ongoing need in the fragrance industry to provide new chemicals to give perfumers and other persons the ability to create new fragrances for perfumes, colognes and personal care products. Those with skill in the art appreciate how differences in the chemical structure of the molecule can result in significant differences in the odor, notes and characteristics of a molecule. These variations and the ongoing need to discover and use the new chemicals in the development of new fragrances allow the perfumers to apply the new compounds in creating new fragrances.

SUMMARY OF THE INVENTION

The present invention provides novel chemicals, and the use of the chemicals to enhance the fragrance of perfumes, toilet waters, colognes, personal products and the like. In addition, the present invention is directed to the use of the novel chemicals to enhance fragrance in perfumes, toilet waters, colognes, personal products and the like.

More specifically, the present invention is directed to the fragrance compounds and a method of improving, enhancing or modifying a fragrance formulation through the addition of an olfactory acceptable amount of dioxaspiro compounds represented by Formula I set forth below:

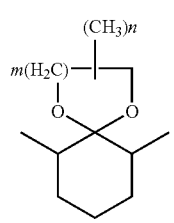

Formula I wherein m is 1 or 2;

and if m is 1, which provides a five-membered dioxaspiro ring, n is an integer from 2 to 4, and the methyl group in the dioxaspiro ring is independently located in the 2 and/or 3 positions of the dioxaspiro ring;

or if m is 2, which provides a six-membered dioxaspiro ring, n is an integer from 0 to 6, and the methyl group in the dioxaspiro ring is independently located in the 2, 3, and/or 4 positions of the dioxaspiro ring.

Another embodiment of the invention is directed to a method for enhancing a perfume composition by incorporating an olfactory acceptable amount of the dioxaspiro compounds provided above.

These and other embodiments of the present invention will be apparent by reading the following specification.

DETAILED DESCRIPTION OF THE INVENTION

In Formulae I above, m is 1 or 2; and if m is 1, which provides a five-membered dioxaspiro ring, n is an integer from 2 to 4, and the methyl group in the dioxaspiro ring is independently located in the 2 and/or 3 positions of the dioxaspiro ring; or if m is 2, which provides a six-membered dioxaspiro ring, n is an integer from 0 to 6, and the methyl group in the dioxaspiro ring is independently located in the 2, 3, and/or 4 positions of the dioxaspiro ring.

It is known to those with the skill in the art that Formula I provides a structure containing five-membered ring when m is 1 and a structure containing a six-membered ring when m is 2.

In another embodiment of the invention, the novel compounds of the invention are represented by the following structures:

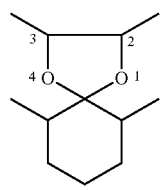

Formula II

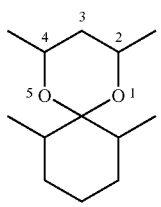

Formula III

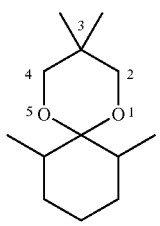

Formula IV

Those with the skill in the art will appreciate that in Formula I:

when m is 1, n is 2, and the methyl groups in the dioxaspiro ring are located in the 2 and 3 positions of the dioxaspiro ring, a compound of Formula II, 2,3,6,10-tetramethyl-1,4-dioxaspiro[4,5]decane, is provided;

when m is 2, n is 2, and the methyl groups in the dioxaspiro ring are located in the 2 and 4 positions of the dioxaspiro ring, a compound of Formula III, 2,4,7,11-tetramethyl-1,5-dioxaspiro[5,5]undecane, is provided; and when m is 2, n is 2, and the methyl groups in the dioxaspiro ring are both located in the 3 position of the dioxaspiro ring, a compound of Formula IV, 3,3,7,11-tetramethyl-1,5-dioxaspiro[5,5]undecane, is provided.

The compounds of the present invention may be prepared via a cyclization reaction of 2,6-dimethyl cyclohexanone, commercially available from Aldrich Chemical Co. with alkane 1, 2 or 1,3 diols. Those with the skill in the art will appreciate that suitable alkane diols include, for example, ethylene glycol, 1,2-propylene glycol, 2,3-butanediol, 2,4-pentanediol, and 2,2-dimethyl propanediol.

The cyclization reaction can be depicted by a general scheme as follows:

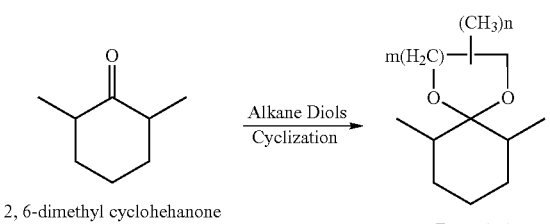

Those with skill in the art will recognize that some of the compounds of the present invention have a number of chiral centers, thereby providing numerous isomers of the claimed compounds. It is intended herein that the compounds described herein include isomeric mixtures of such compounds, as well as those isomers that may be separated using techniques known to those having skill in the art. Suitable techniques include chromatography such as high performance liquid chromatography, referred to as HPLC, and particularly gel chromatography and solid phase microextraction, referred to as SPME. The use of optically active diols such as R-1,2 propane diol as a starting material would afford specific diastereomeric isomers that are contemplated in the present invention.

The use of the compounds of the present invention is widely applicable in current perfumery products, including the preparation of perfumes and colognes, the perfuming of personal care products such as soaps, shower gels, and hair care products as well as air fresheners and cosmetic preparations. The present invention can also be used to perfume cleaning agents, such as, but not limited to detergents, dishwashing materials, scrubbing compositions, window cleaners and the like.

In these preparations, the compounds of the present invention can be used alone or in combination with other perfuming compositions, solvents, adjuvants and the like. The nature and variety of the other ingredients that can also be employed are known to those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

Olfactory effective amount is understood to mean the amount of compound in perfume compositions the individual component will contribute to its particular olfactory characteristics, but the olfactory effect of the perfume composition will be the sum of the effects of each of the perfumes or fragrance ingredients. Thus the compounds of the invention can be used to alter the aroma characteristics of the perfume composition, or by modifying the olfactory reaction contributed by another ingredient in the composition. The amount will vary depending on many factors including other ingredients, their relative amounts and the effect that is desired.

The level of compounds of the invention employed in the perfumed article varies from about 0.005 to about 10 weight percent, preferably from about 0.5 to about 8 and most preferably from about 1 to about 7 weight percent. In addition to the compounds other agents can be used in conjunction with the fragrance. Well known materials such as surfactants, emulsifiers, polymers to encapsulate the fragrance can also be employed without departing from the scope of the present invention.

Another method of reporting the level of the compounds of the invention in the perfumed composition, i.e., the compounds as a weight percentage of the materials added to impart the desired fragrance. The compounds of the invention can range widely from 0.005 to about 70 weight percent of the perfumed composition, preferably from about 0.1 to about 50 and most preferably from about 0.2 to about 25 weight percent. Those with skill in the art will be able to employ the desired level of the compounds of the invention to provide the desired fragrance and intensity.

When used in a fragrance formulation this ingredient provides freshness making the fragrance top notes more desirable and noticeable. It also has a spicy peppery odor which is very commonly used in men's fragrances added for fragrance appropriateness and desirability. The woody part of it is very useful in both men's and women's fragrances adding body and substantivity to the finished product. All of these odor qualities found in this material assist in beautifying and enhancing the finished accord improving the performance of the other materials in the fragrance. The floral of it will beautify as well and makes the fragrance more desirable and add the perception of value. There is also the fruity side of it which is found in many fragrances today which happens to be very trendy, especially for the younger consumer.

The following are provided as specific embodiments of the present invention. Other modifications of this invention will be readily apparent to those skilled in the art. Such modifications are understood to be within the scope of this invention. All starting materials, reagents and catalysts were purchased from Aldrich Chemical Company and used as is. As used herein all percentages are weight percent unless otherwise noted, ppm is understood to stand for parts per million, L is understood to be liter, mL is understood to be milliliter, Kg is understood to be kilogram, g is understood to be gram, and mmHg be millimeters (mm) of mercury (Hg). IFF as used in the examples is understood to mean International Flavors & Fragrances Inc., New York, N.Y., USA.

Example I

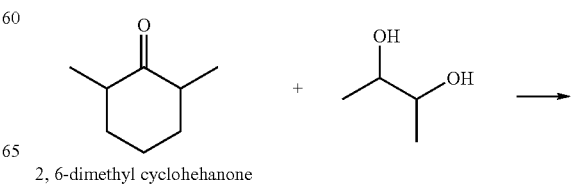

2, 6-dimethyl cyclohehanone

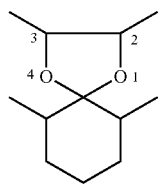

2, 3, 6, 10-tetramethyl-1, 4-dioxaspiro[4, 5]decane

Preparation of 2,3,6,10-tetramethyl-1,4-dioxaspiro[4,5]decane: A reaction flask equipped with a Dean Stark trap was charged with 2,6-dimethyl cyclohehanone (200 g), 2,3-butanediol (315 g), p-toluenesulfonic acid (2 g) and toluene (300 mL). The reaction mass was heated to reflux (110-130° C.). Water (36 mL) was collected in the Dean Stark trap. When no water was recovered the reaction mass was cooled to an ambient temperature, neutralized with 10% aqueous sodium carbonate (100 mL) and washed with brine. Purification by vacuum distillation afforded 2,3,6,10-tetramethyl-1,4-dioxaspiro[4,5]decane (265 g)), which had a boiling point of 104° C. at a pressure of 16 mmHg.

H1 NMR: 0.87-0.96 ppm (m, 6H), 1.1-1.24 ppm (m, 6H), 1.25-1.56 ppm (m, 4H), 1.56-1.91 ppm (m, 4H), 3.55-3.71 ppm (m, 2H)

The compound was described as having a leathery note.

Example II

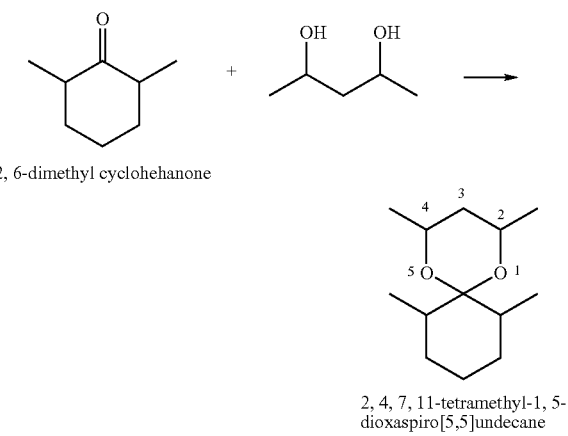

2, 6-dimethyl cyclohehanone 2, 4, 7, 11-tetramethyl-1, 5-dioxaspiro[5,5]undecane Preparation of 2,4,7,11-tetramethyl-1,5-dioxaspiro[5,5]undecane: A reaction flask equipped with a Dean Stark trap was charged with 2,6-dimethyl cyclohehanone (252 g), 2,4-pentanediol (312 g), p-toluenesulfonic acid (6 g) and toluene (300 mL). The reaction mass was heated to reflux (110-130° C.). Water (36 mL) was collected in the Dean Stark trap. When no water was recovered, the reaction mass was cooled to an ambient temperature, neutralized with 10% aqueous sodium carbonate (100 mL) and washed with brine. Purification by vacuum distillation afforded 2,4,7,11-tetramethyl-1,5-dioxaspiro[5,5]undecane (339 g), which had a boiling point of 124° C. at a pressure of 40 mmHg.

H1 NMR: 0.86 ppm (d, 3H, J=6.56 Hz), 0.93 ppm (d, 3H, J=7.23 Hz), 0.99-1.07 ppm (m, 1H), 1.11-1.14 ppm (d, 6H, J=6.97 Hz, of d, J=2.70 Hz), 1.14-1.26 ppm (m, 1H), 1.33-1.59 ppm (m, 6H), 1.60-1.68 ppm (m, 1H), 1.70-1.79 ppm (m, 1H), 3.85-3.91 ppm (m, 1H), 3.91-3.98 ppm (m, 1H)

The compound was described as having a strong chemical solvent note.

Example III

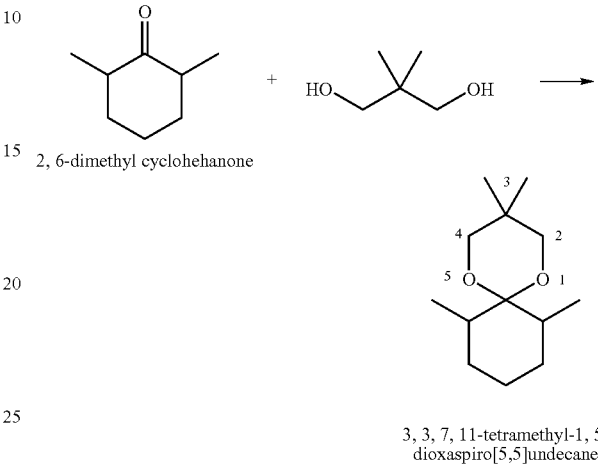

2, 6-dimethyl cyclohehanone 3, 3, 7, 11-tetramethyl-1, 5-dioxaspiro[5,5]undecane Preparation of 3,3,7,11-tetramethyl-1,5-dioxaspiro[5,5]undecane: A reaction flask equipped with a Dean Stark trap was charged with 2,6-dimethyl cyclohehanone (285 g), 2,2-dimethyl propanediol (312 g), p-toluenesulfonic acid (3 g) and toluene (200 mL). The reaction mass was heated to reflux (110-130° C.). Water (36 mL) was collected in the Dean Stark trap. When no water was recovered, the reaction mass was cooled to an ambient temperature, neutralized with 10% aqueous sodium carbonate (100 mL) and washed with brine. Purification by vacuum distillation afforded 3,3,7,11-tetramethyl-1,5-dioxaspiro[5,5]undecane (339 g), which had a boiling point of 124° C. at a pressure of 10 mmHg.

H1 NMR: 0.96 ppm (s, 6H), 0.98 ppm (s, 6H), 1.34-1.61 ppm (m, 8H), 3.44-3.49 ppm (m, 4H)

The compound was described as having a rubbery chemical note.

Example IV

The fragrance formula exemplified as follows demonstrates that dioxaspiro compound imparts a floral woody character to the fragrance formula.

| Ingredients | Parts* + | − |
|---|---|---|
| Caryophyllene | 40.0 | 40.0 |
| Cedarwood White PG | 50.0 | 50.0 |
| Fenchol | 5.0 | 5.0 |
| Healingwood ® | 80.0 | 80.0 |
| Iso E Super ® | 425.0 | 425.0 |
| Methyl beta naphthyl ketone | 2.0 | 2.0 |
| Methyl Ionone Gamma Coeur | 100.0 | 100.0 |
| Patchoulol 4101 LMR | 5.0 | 5.0 |
| Paxamber ® | 100.0 | 100.0 |
| Sanjinol ® | 5.0 | 5.0 |
| Veramoss 10% dipropylene glycol (DPG) | 8.0 | 8.0 |
| Vertofix Coeur | 150.0 | 150.0 |

-continued

| Ingredients | Parts* | |
|---|---|---|
| | + | − |
| 2,3,6,10-Tetramethyl-1,4-dioxaspiro[4,5]decane | 5.0 | — |
| Dipropylene glycol | — | 5.0 |
| Total | 975.0 | 975.0 |

*"+" represents a dioxaspiro compound containing formula; and "−" represents a dioxaspiro compound non-containing formula.

What is claimed is:

1. A compound of Formula I:

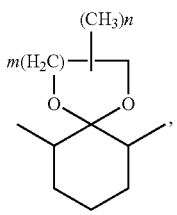

Formula I wherein m is 1 or 2;
and if m is 1, which provides a five-membered dioxaspiro ring, n is an integer from 2 to 4, and the methyl group in the five-membered dioxaspiro ring is independently located in the 2 and/or 3 positions;
or if m is 2, which provides a six-membered dioxaspiro ring, n is an integer from 0 to 6, and the methyl group in the six-membered dioxaspiro ring is independently located in the 2, 3, and/or 4 positions.

2. The compound of claim 1, wherein m is 1, n is 2, and the methyl groups in the five-membered dioxaspiro ring are located in the 2 and 3 positions, and wherein the compound is 2,3,6,10-tetramethyl-1,4-dioxaspiro[4,5]decane.

3. The compound of claim 1, wherein in m is 2, n is 2, and the methyl groups in the six-membered dioxaspiro ring are located in the 2 and 4 positions, and wherein the compound is 2,4,7,11-tetramethyl-1,5-dioxaspiro[5,5]undecane.

4. The compound of claim 1, wherein m is 2, n is 2, and the methyl groups in the six-membered dioxaspiro ring are both located in the 3 position, and wherein the compound is 3,3,7,11-tetramethyl-1,5-dioxaspiro[5,5]undecane.

5. A fragrance product containing an olfactory effective amount of the compound of claim 1.

6. The fragrance product of claim 5, wherein in the compound, m is 1, n is 2, and the methyl groups in the five-membered dioxaspiro ring are located in the 2 and 3 positions, and wherein the compound is 2,3,6,10-tetramethyl-1,4-dioxaspiro[4,5]decane.

7. A method of improving, enhancing or modifying a fragrance formulation through the addition of an olfactory acceptable amount of a compound of Formula I:

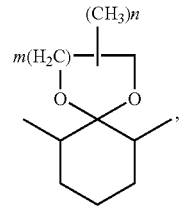

Formula I wherein m is 1 or 2;
and if m is 1, which provides a five-membered dioxaspiro ring, n is an integer from 2 to 4, and the methyl group in the five-membered dioxaspiro ring is independently located in the 2 and/or 3 positions;
or if m is 2, which provides a six-membered dioxaspiro ring, n is an integer from 0 to 6, and the methyl group in the six-membered dioxaspiro ring is independently located in the 2, 3, and/or 4 positions.

8. The method of claim 7, wherein in the compound, m is 1, n is 2, and the methyl groups in the five-membered dioxaspiro ring are located in the 2 and 3 positions, and wherein the compound is 2,3,6,10-tetramethyl-1,4-dioxaspiro[4,5]decane.

9. The method of claim 7, wherein in the compound, m is 2, n is 2, and the methyl groups in the six-membered dioxaspiro ring are located in the 2 and 4 positions, and wherein the compound is 2,4,7,11-tetramethyl-1,5-dioxaspiro[5,5]undecane.

10. The method of claim 7, wherein in the compound, m is 2, n is 2, and the methyl groups in the six-membered dioxaspiro ring are both located in the 3 position, and wherein the compound is 3,3,7,11-tetramethyl-1,5-dioxaspiro[5,5]undecane.

11. The method of claim 7, wherein the fragrance formulation is incorporated into a product selected from the group consisting of a perfume, a cologne, a toilet water, a cosmetic product, a personal care product, a fabric care product, a cleaning product, and an air freshener.

12. The method of claim 11, wherein the cleaning product is selected from the group consisting of a detergent, a dishwashing composition, a scrubbing compound, and a window cleaner.

13. The method of claim 7, wherein the olfactory acceptable amount is from about 0.005 to about 10 weight percent of the fragrance formulation.

14. The method of claim 7, wherein the olfactory acceptable amount is from about 0.5 to about 8 weight percent of the fragrance formulation.

15. The method of claim 7, wherein the olfactory acceptable amount is from about 1 to about 7 weight percent of the fragrance formulation.

16. A fragrance formulation containing an olfactory effective amount of a compound of Formula I:

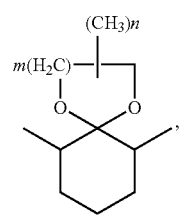

Formula I wherein m is 1 or 2;
and if m is 1, which provides a five-membered dioxaspiro ring, n is an integer from 2 to 4, and the methyl group in the five-membered dioxaspiro ring is independently located in the 2 and/or 3 positions;

or if m is 2, which provides a six-membered dioxaspiro ring, n is an integer from 0 to 6, and the methyl group in the six-membered dioxaspiro ring is independently located in the 2, 3, and/or 4 positions.

17. The fragrance formulation of claim 16, wherein in the compound, m is 1, n is 2, and the methyl groups in the five-membered dioxaspiro ring are located in the 2 and 3 positions, and wherein the compound is 2,3,6,10-tetramethyl-1,4-dioxaspiro[4,5]decane.

* * * * *